(12) United States Patent
Kartaeusch et al.

(10) Patent No.: US 11,841,411 B2
(45) Date of Patent: Dec. 12, 2023

(54) METHOD AND APPARATUS FOR THE RECORDING AND RECONSTRUCTION OF A FOUR-DIMENSIONAL DYNAMIC MAGNETIC RESONANCE IMAGE DATA RECORD

(71) Applicant: Siemens Healthcare GmbH, Erlangen (DE)

(72) Inventors: Ralf Kartaeusch, Erlangen (DE); Simon Bauer, Baunach (DE)

(73) Assignee: Siemens Healthcare GmbH, Erlangen (DE)

( * ) Notice: Subject to any disclaimer, the term of this patent is extended or adjusted under 35 U.S.C. 154(b) by 694 days.

(21) Appl. No.: 16/296,777

(22) Filed: Mar. 8, 2019

(65) Prior Publication Data

US 2019/0274576 A1 Sep. 12, 2019

(30) Foreign Application Priority Data

Mar. 8, 2018 (DE) .......................... 102018203507.5

(51) Int. Cl.
*G01R 33/563* (2006.01)
*A61B 6/00* (2006.01)
*G01R 33/56* (2006.01)

(52) U.S. Cl.
CPC ...... *G01R 33/56308* (2013.01); *A61B 6/5211* (2013.01); *G01R 33/5608* (2013.01)

(58) Field of Classification Search
CPC .... A61B 5/055; A61B 6/5211; G01R 33/5608
See application file for complete search history.

(56) References Cited

U.S. PATENT DOCUMENTS

2007/0167728 A1* 7/2007 Mistretta .............. G01R 33/561
600/410
2009/0041318 A1 2/2009 Feiweier et al.
(Continued)

FOREIGN PATENT DOCUMENTS

CN 101352348 A 1/2009
CN 102283649 A 12/2011
(Continued)

OTHER PUBLICATIONS

Feng, L., et al. "Golden-Angle Radial Sparse Parallel MRI: Combination of Compressed Sensing, Parallel Imaging, and Golden-Angle Radial Sampling for Fast and Flexible Dynamic Volumetric MRI," Magnetic Resonance Medicine. vol. 72(3), 2014. p. 707-717 (Year: 2014).*

(Continued)

*Primary Examiner* — Christopher Koharski
*Assistant Examiner* — Sean A Frith
(74) *Attorney, Agent, or Firm* — Banner & Witcoff Ltd.

(57) ABSTRACT

In a method and apparatus for acquiring and reconstructing a four-dimensional dynamic magnetic resonance (MR) image data record, MR data are continuously acquired by radial scanning of an examination region along radial k-space lines, and a dynamic region of the examination region, in which said dynamic procedure is relevant, is determined, as well as a non-dynamic region, which is not relevant to the dynamic procedure. Static image data are reconstructed from all of the acquired MR data, and image data therein originating from the non-dynamic region are marked and are then not used for reconstructing a dynamic image data record for the dynamic region.

11 Claims, 2 Drawing Sheets

(56) References Cited

U.S. PATENT DOCUMENTS

| | | | |
|---|---|---|---|
| 2011/0091090 A1* | 4/2011 | Dahlqvist Leinhard | G01R 33/4828 382/131 |
| 2014/0303480 A1* | 10/2014 | Lai | A61B 5/055 600/410 |
| 2016/0199004 A1 | 7/2016 | Meyer et al. | |
| 2017/0039738 A1* | 2/2017 | Ziv | A61B 8/5284 |
| 2017/0082715 A1* | 3/2017 | Choi | A61B 5/026 |
| 2017/0325709 A1* | 11/2017 | Nayak | A61B 5/055 |
| 2017/0328974 A1* | 11/2017 | Sanchez Gonzalez | A61B 5/055 |
| 2018/0210055 A1* | 7/2018 | Ding | G01R 23/16 |

FOREIGN PATENT DOCUMENTS

| | | |
|---|---|---|
| CN | 104013403 A | 9/2014 |
| CN | 105769197 A | 7/2016 |
| CN | 106093814 A | 11/2016 |
| CN | 106618571 A | 5/2017 |
| CN | 107209242 A | 9/2017 |

OTHER PUBLICATIONS

Feng, Li et al. "Golden-Angle Radial Sparse Parallel MRI: Combination of Compressed Sensing, Parallel Imaging, and Golden-Angle Radial Sampling for Fast and Flexible Dynamic Volumetric MRI" Magnetic Resonance Medicine; vol. 72; pp. 707-717; 2014 // DOI: 10.1002/mrm.24980.

Rohs Michael et al.: Computergrafik 2: Fourier-Transformation; MHCI Lab, LMU München; pp. 1-66; 2011.

Kalovidouri Anastasia et al.: Fat suppression techniques for breast MRI: Dixon versus spectral fat saturation for 3D T1-weighted at 3 T; Radiol med (2017) 122; pp. 731-742; DOI: 10.1007/s11547-017-0782-2; 2017.

Lin, Wei et al. "Respiratory motion-compensated radial dynamic contrast-enhanced (DCE)-MRI of chest and abdominal lesions" Magnetic Resonance in Medicin, vol. 60, No. 5, pp. 1135-1146, Nov. 2008 // https://doi.org/10.1002/mrm.21740.

Martel, A. L. et al. "Removing undersampling artifacts in DCE-MRI studies using independent components analysis" Magnetic Resonance in Medicine, vol. 59, No. 4, pp. 874-884, Apr. 2008 // https://doi.org/10.1002/mrm.21552.

* cited by examiner

METHOD AND APPARATUS FOR THE RECORDING AND RECONSTRUCTION OF A FOUR-DIMENSIONAL DYNAMIC MAGNETIC RESONANCE IMAGE DATA RECORD

BACKGROUND OF THE INVENTION

Field of the Invention

The invention concerns a method for the recording and reconstruction of a four-dimensional dynamic image data record, in particular perfusion image data record, of an examination region of a patient using a magnetic resonance apparatus, of the type wherein, during a dynamic procedure to be mapped, magnetic resonance data of the examination region are continuously recorded by radial scanning along radial k-space lines, and wherein, for individual time segments of the recording period comprising the dynamic procedure, magnetic resonance images are reconstructed from at least some of the magnetic resonance data allocated to k-space lines recorded during the time segment. In addition, the invention concerns a magnetic resonance apparatus and an electronically readable data carrier that implement such a method.

Description of the Prior Art

Magnetic resonance imaging has become an established imaging modality in medical engineering. While it is possible to use a magnetic resonance apparatus to record static magnetic resonance image data of a patient, dynamic magnetic resonance imaging is also becoming increasingly important. In this context, contrast agents can be used so that by recording the course of the contrast agent concentration, information regarding the dynamic procedure within a patient can be obtained. One example of a specific imaging recording in the context of dynamic magnetic resonance imaging is the measurement of liver perfusion.

Since the recording of magnetic resonance data requires a certain amount of time, for example for the recording of k-space line in a memory organized as k-space that is to be scanned (filled with data entries), one challenge in dynamic magnetic resonance imaging is to enable as good a coverage of k-space as possible in time segments that are as short as possible. This is particularly the case in the rapidly variable portions of the dynamic procedure. For this purpose, radial scanning techniques for scanning k-space can be considered, as these can be selected, in particularly spaced apart from one another by the golden angle, so that even a few k-space lines enable as uniform a scanning of k-space as possible. It has therefore been specifically proposed, during the dynamic procedure. With a contrast agent flowing through the examination region, to continuously record magnetic resonance data along different radial k-space lines (often referred to as spokes). An exemplary measurement and reconstruction method, which uses radial scanning of this kind with a scanning model based on the golden angle, is GRASP (Golden-Angle Radial Sparse Parallel MRI—see for example the article by Li Feng et al., "Golden-Angle Radial Sparse Parallel MRI: Combination of Compressed Sensing, Parallel Imaging, and Golden-Angle Radial Sampling for Fast and Flexible Dynamic Volumetric MRI", Magn Reson Med 72 (2014), pages 707-717). In such substantially continuous recordings of radial k-space lines (spokes), it is possible to decide how many of said spokes are used for a magnetic resonance image at the time of reconstruction.

In the case of particularly rapidly occurring dynamic procedures, i.e. higher dynamics, the number of radial k-space lines that are used for a reconstruction must be selected as low as possible, in order to obtain a high temporal resolution. As a consequence of the resulting underscanning, however, artifacts may occur, in particular streaking artifacts. The cause of such streaking artifacts can usually be found in the edge region of the imaging region, therefore the edge region of the homogeneity volume. Streaking artifacts often arise with a large magnitude, meaning that a diagnostic image quality is no longer present. One example of the cause of such streaking artifacts is signals originating from the arms of the patient. Therefore, in general the intensity of the artifacts is highly dependent upon the patient geometry/position of the patient.

It has therefore been proposed in the prior art to strive to position the patient optimally in the patient aperture of the magnetic resonance scanner. A further approach uses specifically designed saturation pulses to suppress, at the point of excitation, the magnetic resonance signal from regions that are problematic for artifacts. In this context, two options are conceivable, namely global fat saturator pulses, or local saturation pulses, which do not necessarily need to relate to fat. With regard to the arms of patient, which are at the periphery of the imaging volume, fat saturation is only functional to a limited extent due to the increasingly inhomogeneous basic magnetic field in the edge region of the patient tunnel. An alternative approach would be to make use of more radial k-space lines for reconstruction of a magnetic resonance image, but the temporal resolution would then be reduced and the dynamic procedure therefore becomes more poorly depictable.

SUMMARY OF THE INVENTION

An object of the invention is to provide an option for the artifact-reduced, highly temporally resolved reconstruction of a dynamic image data record.

This object in a method of the type mentioned in the introduction wherein, according to the invention, the examination region is divided into a dynamic region, in which the dynamic procedure takes place, and a non-dynamic region outside the dynamic region, wherein a static image data record is reconstructed from all recorded magnetic resonance data. In this static image data record image data originating from the non-dynamic region are marked so as to be eliminated from the magnetic resonance data by inverse transformation of that image data, and the magnetic resonance images of the different time segments are reconstructed from the magnetic resonance data modified in this manner. The contents of the magnetic resonance images are used for the compilation of the dynamic image data record in the dynamic region.

The invention is based on the insight that the streaking artifacts are the result of the required high underscanning, which is necessary for depicting the dynamics in the dynamic image data record. However, the outer regions, hence the non-dynamic region, from which the streaking artifacts result, are not of interest for the diagnostics. The invention therefore supplements the previous reconstruction, by using two steps. In an additional reconstruction step, data from all points in time are reconstructed to form a static image data record, for which, therefore, no further underscanning is required. In this manner, the static portion of the magnetic resonance signal can be determined from the critical non-dynamic region. The static image data record, and thus also the image data of the non-dynamic region, are normally free from streaking artifacts, but of course no longer show the dynamic procedure, because only a single volume is compiled over the entire recording period.

If the image data that originate from the non-dynamic region, and are therefore irrelevant for the dynamic procedure to be mapped, are first identified in the static image data record, correction data are able to be generated by an inverse transformation into k-space. The correction data are accordingly able to be removed from the magnetic resonance data (raw data in k-space), by subtraction. When the magnetic resonance data modified in this manner, from which the image data of the non-dynamic region can therefore be eliminated, are now reconstructed, the dynamic procedure can be depicted in a considerably artifact-reduced manner, since the streaking artifacts from the critical regions in the non-dynamic region cannot arise, or can only arise to a reduced extent. The removal of magnetic resonance data from regions of the examination region responsible for streaking artifacts therefore leads to a significant reduction of artifacts and, most of all, to a stabilization of the measurement results even over many different patients.

In this context, the dynamic image data record in principle can be determined limited to the dynamic region, so that the magnetic resonance images of the dynamic image data record show only the dynamic region with the contents, which are accordingly reconstructed there from the modified magnetic resonance data. It is also possible (and preferable) for the magnetic resonance images of the dynamic image data record in the non-dynamic region to use the image data of the static image data record. Since the dynamic procedure to be mapped does not take place in the non-dynamic region, and artifact-free, high-quality data of the non-dynamic region only present because of the underscanning due to the static image data, it is therefore possible to use it in the magnetic resonance images. In the dynamic region, by contrast, the reconstruction results from the magnetic resonance data purged of the correction data originating from the non-dynamic region, which likewise supplies artifact-reduced reconstruction results, so that overall high-quality magnetic resonance images occur with a good possibility for orientation.

In an embodiment of the invention, the dynamic region and the non-dynamic region are determined by evaluating the static image data record by localization and marking of at least some of the anatomical features not related to the dynamic procedure. Alternatively or additionally, an item of saturation information can be used, in particular derived from recording parameters, which describes the positioning of a saturation region in the magnetic resonance sequence used. If, in the course of the magnetic resonance sequence used for recording the magnetic resonance data, a saturation technique is also used which is likewise already intended to contribute to avoiding anatomical features resolving contributions from streaking artifacts and/or other artifacts, therefore from the non-dynamic region, then the position of such "saturators" may already considerably indicate sites from where no magnetic resonance data relating to the dynamic procedure is expected. Accordingly, this saturation information can be used to identify the image data of the non-dynamic region in the static image data record. In this context, the positioning of such saturation regions can take place at least partially automatically, for example on the basis of a localizer, and/or at least partially in a user-controlled manner.

Alternatively, or preferably additionally, it is also possible to carry out an image evaluation of the static image data record, for example a reconciliation, with an anatomical atlas and/or by using another labeling method, in order to be able to identify anatomical features that are not related to the dynamic procedure. For example, the arms of the patient thus can be localized in the static image data record and marked accordingly. Corresponding evaluation algorithms for segmentation and/or identification of anatomical features in image data records of magnetic resonance are known, and so do not need to be explained in greater detail herein.

The image data of the non-dynamic region, which has been inverse-transformed into k-space, can be removed from the magnetic resonance data by subtraction. In this context, during the inverse transformation and during the removal from the magnetic resonance data, it is of course also necessary to consider measures carried out in addition to a fast Fourier Transform (FFT), in particular accordingly during the inverse transformation. This may relate not only to various filtering measures, but also to measures for conversion into a Cartesian grid, in particular during the radial scanning. In this context, the method of "gridding" is known for example. During the gridding reconstruction, an interpolation of the radially scanned magnetic resonance data is carried out on a Cartesian grid. This can be followed by a scanning density correction, wherein furthermore, following the fast Fourier Transform in the image space, the effect of the interpolation kernel is also able to be corrected. In order to be able to process the magnetic resonance data and the inverse-transformed image data of the non-dynamic region, i.e. the correction data, in a combined manner, these must be present at corresponding scanning points. For this purpose, the steps of a gridding reconstruction are able to be back-calculated in their entirety, in order to work at the radial scanning points. It is also possible to work in the already recalculated region, i.e. on the Cartesian scanning grid in k-space. Due to the measures that have been carried out, care must be taken that filtering takes place correctly in order to actually extract the correct data.

Additional filter measures regarding the image data or the correction data are also possible, for example with regard to an introduction of at least some of the dynamics of the magnetic resonance data into the static calculations of the correction data.

In an embodiment of the invention, successively scanned k-space lines are spaced apart by the golden angle. Therefore, it is possible for the GRASP technique to be used in the context of the present invention, which uses precisely this spacing by the golden angle in order to enable as uniform a scanning of k-space as possible, even with a low number of singled-out k-space lines (spokes).

As a dynamic procedure, contrast agent movement can be measured, in particular in the liver as part of the dynamic region and/or with the arms as part of the non-dynamic region. An important application of the method according to the invention is in perfusion procedures, which can be implemented with the administration of contrast agent as a dynamic procedure, for example. The dynamics then relate to the course of the contrast agent concentration in at least one anatomical feature of interest, for example the liver, if a liver perfusion measurement is to be performed. In the region of the torso, the arms of the patient in particular are relevant as a cause of streaking artifacts.

The invention also concerns a magnetic resonance apparatus having a control computer designed to carry out the method according to the invention. The control computer can have at least one processor and at least one memory. In addition to a known sequence controller for the implementation of magnetic resonance sequences for the recording of magnetic resonance data, the control computer has a reconstruction processor for the reconstruction of the static image data record, a marking unit for the identification of image data originating from the non-dynamic region in the static image data record, a correction processor for the determination of modified magnetic resonance data, from which the correction data, i.e. the inverse-transformed image data of the non-dynamic region, can be eliminated. The control computer also has at least one further reconstruction processor for the determination of the dynamic image data record. All the statements relating to the method according to the invention apply analogously to the magnetic resonance apparatus according to the invention, and therefore the advantages already described are obtained by the apparatus.

The present invention also encompasses a non-transitory, computer-readable data storage medium encoded with programming instructions that, when the storage medium is loaded into a computer or computer system of an magnetic resonance apparatus, cause the computer or computer system to operate the magnetic resonance apparatus so as to implement any or all embodiments of the method according to the invention, as described above.

DESCRIPTION OF THE PREFERRED EMBODIMENTS

The following section describes an exemplary embodiment of the present invention regarding the determination of a dynamic image data record of a patient, which is intended to show liver perfusion. In order to be able to map the liver perfusion as a dynamic procedure in the dynamic magnetic resonance imaging, the patient is administered with a contrast agent and the course of the contrast agent concentration in the liver of the patient is measured.

Figure 1:
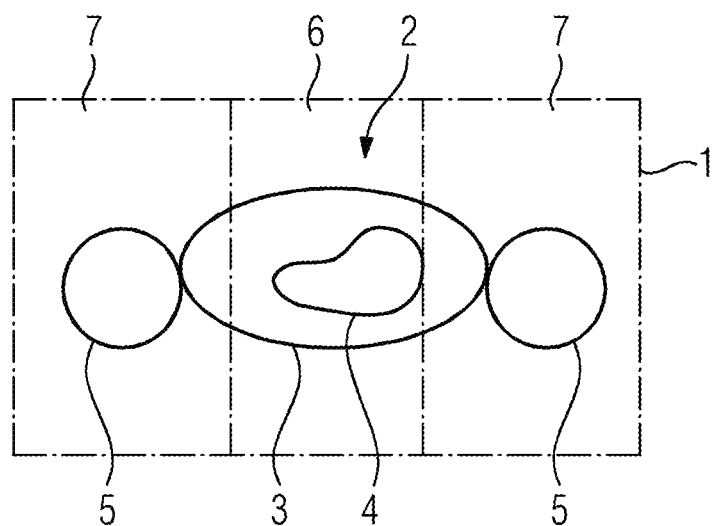
FIG. 1 shows a cross-section through an examination region of a patient.

In this context, FIG. 1 shows, as an example, the examination region 1 that arises during the radial scanning used here, which is substantially the entire patient 2 (shown in a cross-section). For the dynamic procedure that is to be implemented, only the torso 3 with the liver 4 is visible and relevant; no dynamic procedure to be measured takes place in the arms 5, which lie in the outer regions in which the homogeneity of the magnetic fields of the magnetic resonance device is already limited. The examination region 1 therefore can be divided into a dynamic region 6 and a non-dynamic region 7, which here is formed by the outer regions that include the arms 5.

Figure 2:
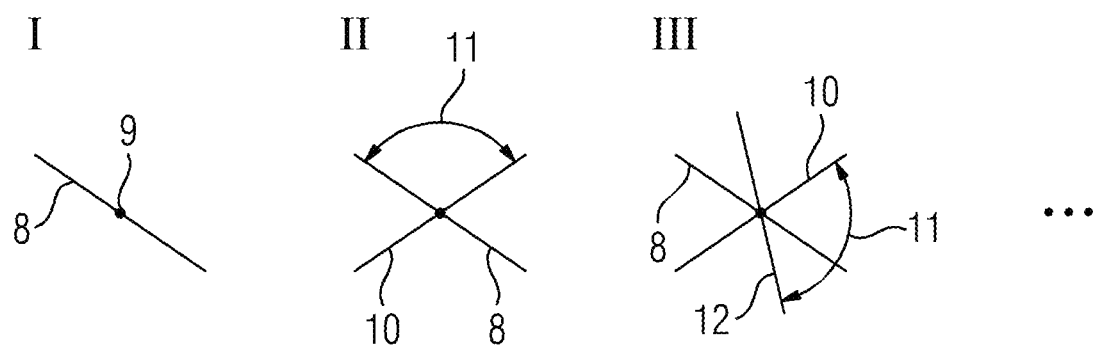
FIG. 2 is a schematic diagram for the continuous recording of radial k-space lines in the golden angle model.

In the present case a GRASP technique is used for the continuous recording of magnetic resonance data, in order to measure the dynamic procedure. Radial scanning of k-space takes place, wherein a golden angle model is used, as indicated in FIG. 2. Here, the first radial k-space line 8 to be measured runs through k-space center 9, as can be seen under I. Subsequently, see II, a second radial k-space line 10 is measured, which is rotated by a golden angle 11, here 111.25°, with respect to the radial k-space line 8. Accordingly, in turn, the third k-space line 12, see III, is measured with a rotation by the golden angle 11 from the direction of the second radial k-space line 10, and so on.

This results in an excellent uniform coverage of k-space even when extracting only a few of the radial k-space lines 8, 10, 12, as is necessary in order to map dynamic procedures with a higher temporal resolution.

This means that, in order to define the individual magnetic resonance images of the dynamic image data record, magnetic resonance data lying within a time segment with certain few k-space lines 8, 10, 12 are always singled out in order to reconstruct the corresponding magnetic resonance image. There is therefore an underscanning, in which streaking artifacts may arise. The causes thereof mostly lie, as has been recognized, outside the relevant dynamic region 6, i.e. in the non-dynamic region 7, and are therefore produced by the arms 5 in particular.

In the method according to the invention, image data are identified that are to be allocated to the non-dynamic region, so as to transform that data back into k-space, and there to eliminate that data from the magnetic resonance data. Therefore, when reconstruction of magnetic resonance images takes place, fewer streaking artifacts, even from few k-space lines 8, 10, 12 occur, because the causes thereof have for the most part been removed.

Figure 3:
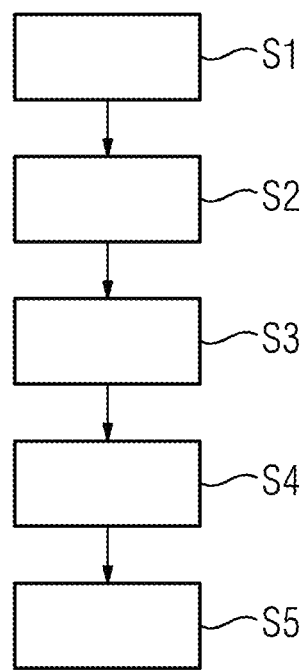
FIG. 3 is a flowchart of an exemplary embodiment of the method according to the invention.

FIG. 3 shows a flowchart of an exemplary embodiment of the method according to the invention.

Here, in a step S1 during the dynamic procedure, i.e. the contrast agent throughflow in this case, magnetic resonance data are continuously recorded by radial scanning along k-space lines 8, 10, 12 rotated with respect to one another by the golden angle.

Following this, the reconstruction phase begins, wherein initially a reconstruction of a static image data record takes place in step S2, from all the recorded magnetic resonance data of all k-space lines 8, 10, 12.

There is therefore no underscanning, and streaking artifacts are improbable. In a step S3, image data of the non-dynamic region 7 are identified in the static image data record. Two approaches, which can be used individually or in combination, are possible. One possibility is to already deduce the position of the non-dynamic regions 7 from the positioning of saturation regions, in which a fat saturation technique or another saturation technique (local saturators) has been applied during the recording in step S1. Another possibility is to evaluate the static image data record so as to identify the location of anatomical features, for example the arms 5, in which the dynamic procedure does not take place (or only with a significant reduction).

In a step S4, the image data of the non-dynamic region 7 are inverse-transformed into k-space, wherein steps of a gridding reconstruction and corresponding filtering operations are implemented, in order to subsequently achieve a removal of the correction data, which has been obtained in this manner, from the magnetic resonance data by subtracting the correction data from the magnetic resonance data. This can take place in k-space at the actual radial scanning points, but also on a Cartesian grid (after a regridding).

In a step S5, the magnetic resonance images of the dynamic image data record are then determined by a reconstruction from the modified magnetic resonance data of step S4 taking place in the dynamic region 6. For the non-dynamic region 7, in which the dynamic procedure to be mapped does not take place in any case, use is made of the image data of the static image data record in order to achieve an orientation. Of course, it is also possible to restrict the magnetic resonance images to the dynamic region 6.

Figure 4:
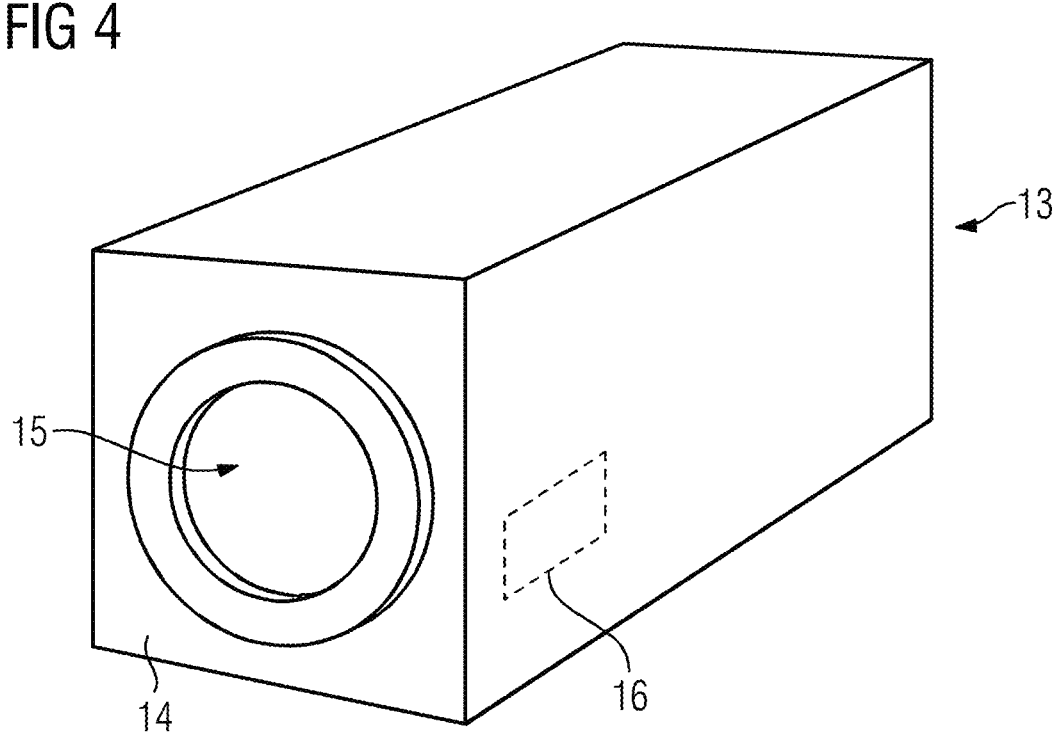
FIG. 4 schematically illustrates a magnetic resonance device according to the invention.

FIG. 4 shows a magnetic resonance apparatus 13 according to the invention. This has a scanner 14 with a basic field magnet 14 which defines a patient aperture 15, into which a patient can be introduced by a patient bed (not shown). A radio-frequency (RF) coil arrangement and a gradient coil arrangement (not shown) surround the patient aperture 15.

The operation of the magnetic resonance apparatus 13 is controlled by a control computer 16, which is configured to perform the method according to the invention. To this end, the control computer 16 have suitable reconstruction processors, a marking processor and a correction processor.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for acquiring and reconstructing a four-dimensional dynamic magnetic resonance (MR) image data record of an examination region of a patient, said method comprising:
   from a computer, operating an MR data acquisition scanner so as to execute a dynamic MR data acquisition procedure wherein MR data of an examination region of a patient are continuously acquired, and entered into a memory organized as k-space, by radial scanning of k-space along respective radial k-space lines;
   in said computer, during respective individual time segments of a recording period during which said MR data are acquired in said dynamic data acquisition procedure, reconstructing respective MR images from at least some of the acquired MR data respectively in said k-space lines into which said MR data were entered during the respective time segment;
   in said computer, determining a dynamic region and a non-dynamic region by evaluating a position of a saturation region in an MR data acquisition sequence that is used to acquire said MR data;
   in said computer, dividing said examination region spatially into said dynamic region, in which said dynamic data acquisition procedure takes place, and said non-dynamic region outside of said dynamic region, and reconstructing a static MR image data record that is a combination of MR data acquired in a plurality of the individual time segments, marking, in said static MR image data record, image data that originate from said non-dynamic region, performing an inverse transformation of the marked image data in said static MR data record, and creating respective modified MR data by eliminating marked image data from said MR data; and
   in said computer, reconstructing MR images for said respective time segments from modified MR data so as to compile a dynamic image data record in said dynamic region.

2. A method as claimed in claim 1 comprising using image data in a static image data record for the MR images of the dynamic image data record in said non-dynamic region.

3. A method as claimed in claim 1 comprising determining said dynamic region and said non-dynamic region by evaluating the static image data record, by localization and marking of at least some anatomical features of the patient that are unrelated to the dynamic data acquisition procedure.

4. A method as claimed in claim 1 comprising removing said marked image data that were inverse transformed into k-space, of said non-dynamic region, by subtraction.

5. A method as claimed in claim 4 comprising removing said inverse-transformed image data in k-space after implementing a Cartesian gridding, so that said inverse-transformed image data are in a Cartesian grid, and recalculating the MR data in said Cartesian grid.

6. A method as claimed in claim 4 comprising removing the inverse-transformed image data in k-space at scanning points used in said radial scanning of k-space.

7. A method as claimed in claim 1 comprising spacing successively scanned radial lines in k-space apart from each other by the golden angle.

8. A method as claimed in claim 1 comprising administering a contrast agent to the patient before executing said dynamic data acquisition procedure and acquiring said MR data from the liver of the patient, as said examination region.

9. A method as claimed in claim 1 comprising determining said non-dynamic region to be a region of the patient consisting of the arms of the patient.

10. A magnetic resonance (MR) apparatus comprising:
    an MR data acquisition scanner;
    a computer configured to operate said MR data acquisition scanner so as to execute a dynamic MR data acquisition procedure wherein MR data of an examination region of a patient are continuously acquired, and entered into a memory organized as k-space, by radial scanning of k-space along respective radial k-space lines;
    said computer being configured to reconstruct, during respective individual time segments of a recording period during which said MR data are acquired in said dynamic data acquisition procedure, respective MR images from at least some of the acquired MR data respectively in said k-space lines into which said MR data were entered during the respective time segment;
    said computer being configured to determine a dynamic region and a non-dynamic region by evaluating a position of a saturation region in an MR data acquisition sequence that is used to acquire said MR data;
    said computer being configured to divide said examination region spatially into said dynamic region, in which said dynamic data acquisition procedure takes place, and said non-dynamic region outside of said dynamic region, and to reconstruct a static MR image data record that is a combination of MR data acquired in a plurality of the individual time segments, to mark, in said static MR image data record, image data that originate from said non-dynamic region, to perform an inverse transformation of the marked image data in said static MR data record, and create respective modified MR data by eliminating marked image data from said MR data; and
    said computer being configured to reconstruct MR images for said respective time segments from modified MR data so as to compile a dynamic image data record in said dynamic region.

11. A non-transitory, computer-readable data storage medium encoded with programming instructions, said storage medium being loaded into a computer of a magnetic resonance (MR) apparatus, and said programming instructions causing said computer to:
    operate said MR apparatus so as to execute a dynamic MR data acquisition procedure wherein MR data of an examination region of a patient are continuously acquired, and entered into a memory organized as k-space, by radial scanning of k-space along respective radial k-space lines;
    during respective individual time segments of a recording period during which said MR data are acquired in said dynamic data acquisition procedure, reconstruct respective MR images from at least some of the acquired MR data respectively in said k-space lines into which said MR data were entered during the respective time segment;

determine a dynamic region and a non-dynamic region by evaluating a position of a saturation region in an MR data acquisition sequence that is used to acquire said MR data;

divide said examination region spatially into said dynamic region, in which said dynamic data acquisition procedure takes place, and said non-dynamic region outside of said dynamic region, and reconstruct a static MR image data record that is a combination of MR data acquired in a plurality of the individual time segments, mark, in said static MR image data record, image data that originate from said non-dynamic region, perform an inverse transformation of the marked image data in said static MR data record, and create respective modified MR data by eliminating marked image data from said MR data; and reconstruct MR images for said respective time segments from modified MR data so as to compile a dynamic image data record in said dynamic region.

* * * * *